United States Patent [19]

Oyama et al.

[11] 4,072,678

[45] Feb. 7, 1978

[54] PROCESS FOR PRODUCING CAPROLACTAM

[75] Inventors: Fusao Oyama; Sadatomi Murao; Shizuo Okada, all of Niihama, Japan

[73] Assignee: Sumitomo Chemical Company, Limited, Osaka, Japan

[21] Appl. No.: 698,122

[22] Filed: June 21, 1976

[30] Foreign Application Priority Data

June 24, 1975 Japan ................................. 50-79198

[51] Int. Cl.$^2$ .......................................... C07D 201/04
[52] U.S. Cl. .............................................. 260/239.3 A
[58] Field of Search .............. 260/239.3 A; 423/451 A

[56] References Cited

U.S. PATENT DOCUMENTS

| 2,973,355 | 2/1961 | Bauer | 260/239.3 A |
| 3,264,060 | 8/1966 | Nieswandt et al. | 260/239.3 A |
| 3,795,731 | 3/1974 | Furkert | 423/541 A |
| 3,852,272 | 12/1974 | De Rooij | 260/239.3 A |
| 3,852,273 | 12/1974 | De Rooij | 260/239.3 A |
| 3,954,955 | 5/1976 | Furkert | 423/541 A |
| 3,992,372 | 11/1976 | Gath et al. | 260/239.3 A |
| 4,036,830 | 7/1977 | De Rooij et al. | 260/239.3 A |

FOREIGN PATENT DOCUMENTS

| 557,462 | 5/1958 | Canada | 260/239.3 A |

*Primary Examiner*—Henry R. Jiles
*Assistant Examiner*—Robert T. Bond
*Attorney, Agent, or Firm*—Cushman, Darby & Cushman

[57] ABSTRACT

Treatment of process waste waters to be discharged from a lactam manufacturing plant by stepwise concentration in two steps under suitable conditions, extraction of lactam from the concentrate with an organic solvent, oxidative combustion of the extract residue and conversion of sulfur dioxide formed into sulfuric acid can save losses of lactams, organic solvents and sulfur containing compounds to a considerable extent and render the waste waters no longer harmful.

9 Claims, 1 Drawing Figure

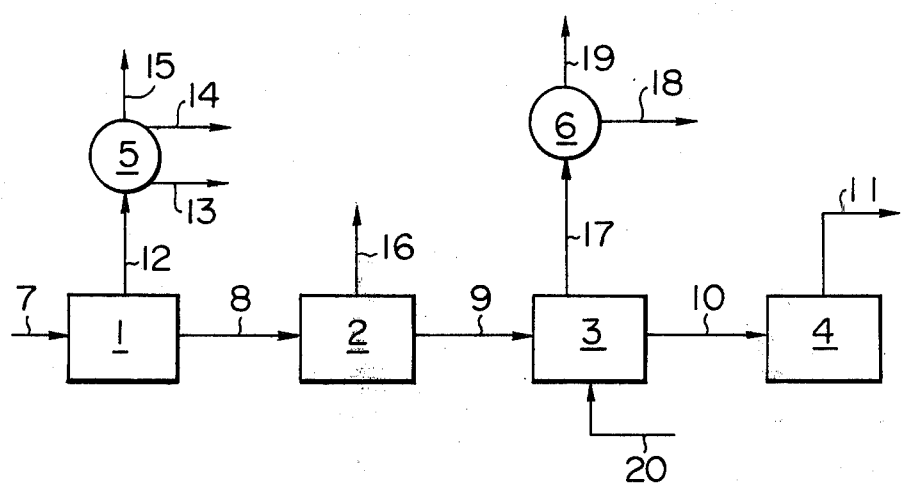

PROCESS FOR PRODUCING CAPROLACTAM

This invention relates to an improved process for producing lactams. More particularly, this invention pertains to a process for producing lactams improved in that useful components are recovered from process waste waters simultaneously with conversion of residues into harmless compounds by specific treatment of process waste waters discharged from the step of producing lactams.

Lactams (e.g. ε-caprolactam) are generally produced by submitting cycloalkanone oximes (e.g. cyclohexanone oxime) to Beckmann rearrangement by use of a concentrated sulfuric acid or fuming sulfuric acid, neutralizing the rearranged mixture with ammonia, followed by removal of ammonium sulfate from the neutralized product through stratification, then extracting lactams with a suitable solvent from the remaining layer and purifying the extract by distillation. In this process, the process waste waters obtained thereby as extract residues generally contain caprolactam, organic solvents, ammonium sulfate, water-soluble organic impurities containing sulfur, etc. Various troubles can be expected to be caused from the standpoint of prevention of environmental pollution when such waste waters are permitted to be discarded into the river or sea with no treatment. In addition, disposal of such waste waters accompanies losses of lactams which are the main products and the organic solvents used for extraction to result in economical disadvantage of the process.

The principal object of the present invention is to provide a process for producing lactams which reduces the drawbacks of the prior art as mentioned above.

The present invention provides a process for producing lactams by effecting Beckmann rearrangement of alkanone oximes with a concentrated sulfuric acid or fuming sulfuric acid, neutralizing the rearranged mixture with ammonia and separating ammonium sulfate and lactams from the resulting product, wherein the improvement comprises treating the waste waters after separation of said ammonium sulfate and lactams in accordance with the following steps:

(1) first concentrating by distillation the waste waters to a water concentration in the range from 85 to 75 wt.%;

(2) then further concentrating by distillation the concentrate thus obtained to a water concentration in the range from 70 to 15 wt.%;

(3) extracting lactams from the thus obtained concentrate with an organic solvent thereby to recover lactams;

(4) conducting oxidative combustion of the extract residue; and (5) converting the thus formed sulfur dioxide to sulfuric acid.

The present invention is inclusive of the embodiment wherein organic solvents contained in the distillates obtained from the concentration steps as mentioned above are recovered for reuse and also of the embodiment wherein sulfuric acid is produced by conventional method from the sulfur dioxide formed in the combustion step and recycled to the rearrangement step.

In order that the present invention can readily be carried into effect, reference is now made to the accompanying drawing which shows a schematic flow diagram of the steps suitable for practicing the process of the invention, in which 1 and 2 show concentration steps, 3 extraction step, 4 combustion step, 5 condensation step, 6 step for separation of solvent, and 7 through 20 lines, respectively.

The waste waters after separation of ammonium sulfate and lactams as mentioned above are fed to the concentration step 1 through line 7. The distillate from the concentration step 1 is introduced into the condensation step 5 through line 12. Organic solvents recovered by separation after condensation treatment may be provided for use in extraction of lactams. The condensed water withdrawn from line 13 can either be used in other uses or discarded. The sulfur dioxide, if present in the distillate, is discharged from line 15 and may be subjected to combustion treatment by being absorbed in the waste waters to be fed into the combustion step 4 as mentioned below or alternatively be converted to sulfuric acid by being incorporated into the gas discharged after said combustion treatment. The thus concentrated waste liquor from the step 1 is then fed to the other concentration step 2 through line 8 to be further concentrated. The distillate from the step 2 withdrawn through line 16 consists substantially of water and, after being condensed, may either be discarded or utilized as processing water. The waste waters concentrated in the step 2 are fed through line 9 to the extraction step 3, wherein extraction treatment is carried out with the organic solvent supplied through line 20 to separate lactams contained in the waste waters by extraction. The extract mixture is withdrawn through line 17 and introduced into the separation step 6 wherein separation is conducted by conventional methods such as distillation. The lactam separated is recovered through line 18 and the organic solvent separated through line 19 to be recycled for reuse. The residue after extraction of the lactam is introduced through line 10 into the combustion step 4. The sulfur dioxide formed by the oxidative combustion of extraction residue is converted by conventional method via sulfuric anhydride into sulfuric acid or fuming sulfuric acid. The thus formed sulfuric acid can be used in the rearrangement step in the procedure for producing lactams.

In the present invention, it is critically required that the concentration of the waste waters should be conducted in two steps. If it is conducted by one step, organic solvents contained in the waste waters can be separated with difficulty. In addition, it is also difficult to utilize effectively the distillates produced, especially steam. On the other hand, concentration treatment by three or more steps is economically disadvantageous in view of installation costs.

The concentration treatment in the first step is conducted desirably at a temperature ranging from about 80° to 130° C under a pressure ranging from 400 mm Hg to 2.7 Kg/cm². If the concentration temperature under a pressure within said range is lower than the range as specified above, it is difficult to separate the organic solvents from the waste waters and the distillates obtained are often disadvantageous in utilization as heat source for the second concentration step. On the contrary, if the temperature exceeds said range, lactams contained in the waste waters may undergo polymerization to result in losses or deterioration in quality of the lactams recovered from the subsequent step. Furthermore, unfavorable results in aspect of corrosion of equipment materials are liable to be caused at a too high temperature. The extent of concentration in the first step is required to be in the range from 85 to 75 wt.%; in terms of the water concentration. If the extent of concentration is too low, i.e. over 85 wt.% water concentration, there are disadvantages in thermal efficiency as well as in a difficult separation procedure by stratification when organic solvents are recovered from condensed distillates. On the contrary, if it is too high, i.e. less than 75 wt.% water concentration, the procedure is also disadvantageous in thermal efficiency and the concentration of sulfur dioxide formed by decomposition of ammonium sulfate is so high that unfavorable results are liable to be caused by corrosion of equipment materials.

The second concentration step is carried out desirably at a temperature ranging from about 40° to 80° C under a pressure ranging from 50 to 400 mmHg until the water concentration becomes 70 to 15 wt.%. If the temperature is lower than said range under a pressure in the specified range, it is difficult to maintain an appropriate temperature at the time of extraction treatment of lactams in the next step, whereby decrease in extraction efficiency is caused. On the other hand, if the temperature is higher than said range, the extraction operation cannot smoothly be carried out since it is close to the boiling point of the organic solvent to be used in the extraction step as mentioned above. Furthermore, a lower extent of concentration than the range as specified above will cause decrease in recovery of lactams in the next extraction step. When the extent of concentration is higher than said range, precipitation of ammonium sulfate contained in the waste waters is liable to occur, whereby not only decrease in efficiency of the process is effected, but also bad influences will be affected on the quality of lactams recovered. In particular, as often effectively is practiced, when the heat source of the distillates from the first concentration step is utilized as a heat source for the second concentration step, the concentration conditions should be controlled in the manner as described above from the standpoint of improvement in utility efficiency of heat.

The organic solvents to be used in the extraction step may be those known in the art as lactam extraction solvents, typically aromatic hydrocarbon such as benzene, toluene and the like. The amount of the solvents as well as the extraction conditions are not specifically limited but conventional methods can be feasible. In order to prevent the extracting agent and the liquid to be extracted from forming emulsions, the pH of the liquid to be extracted is preferably controlled at about 2.5 to about 6.

A small amount of organic solvents contained in the extract residue is preferably recovered by evaporation before the residue is charged into the combustion step. The combustion is performed desirably at a temperature ranging from about 800° to 1300° C. The combustion is carried out by charging sulfur simultaneously with oxygen or molecular oxygen containing gas. If desired, they may directly be supplied to a sulfur burning furnace for production of sulfur dioxide. If the combustion temperature is lower than 800° C, no complete combustion can be effected, while unfavorable formation of nitrogen oxides is observed when the temperature is higher than 1300° C.

Thus, the process of the invention can bring about various advantages by treatment of the waste waters discharged out from the lactam manufacturing plants as mentioned above, namely:

a. recovery of lactams and organic solvents in high yields;

b. decrease in losses in the production steps of lactams by recovery of ammonium sulfate and sulfur containing organic compounds in the form of sulfuric acid;

c. recycle for reuse of the thus recovered organic solvents and sulfuric acid;

d. no discharge of harmful waste waters; etc.

The present invention is illustrated in further detail by referring to the following Example, which is set forth for not limiting but illustrative purpose. Unless otherwise noted, all percentages are by weight.

EXAMPLE 1

Cyclohexanone oxime was subjected to Beckmann rearrangement by using fuming sulfuric acid. The rearranged mixture was neutralized with ammonia. After removal of ammonium sulfate by stratification from the neutralized product, followed by separation of caprolactam by benzene extraction, the waste waters obtained was treated in accordance with the flow as shown in the accompanying drawing to obtain the result as shown in the following Table.

| No. in the drawing | Flow amount Kg/H | Pressure mm Hg | Temperature (° C) | Composition (%) | | | |
|---|---|---|---|---|---|---|---|
| | | | | Caprolactam | Benzene | All S content | Water |
| 1 | — | 840 | 101 | — | — | — | — |
| 2 | — | 100 | 54 | — | — | — | — |
| 3 | — | 760 | 60 | — | — | — | — |
| 4 | — | 760 | 1100 | — | — | — | — |
| 7 | 90 | — | — | 0.4 | 0.15 | 1.3 | 90.0% |
| 8 | 54 | | | 0.7 | 0 | 2.1 | 83.5% |
| 9 | 18 | | | 2.0 | 0 | 6.5 | 50.5% |
| 10 | 17.7 | — | — | 0.2 | 0 | 6.5 | 51.4% |
| 12 | 36 | — | — | — | — | — | — |
| 13 | 35.9 (water) | — | — | — | — | — | — |
| 14 | 0.1 (benzene) | — | — | — | — | — | — |
| 16 | 36 (water) | — | — | — | — | — | — |
| 17 | 80.3 | — | — | — | — | — | — |
| 18 | 0.3 (caprolactam) | — | — | — | — | — | — |
| 19 | 80 (benzene) | — | — | — | — | — | — |
| 20 | 80 (benzene) | — | — | — | — | — | — |

Notes)
(a) The sulfur dioxide containing gas withdrawn from line 15 was mixed into line 11 in a concentration of 65 vol.%.
(b) The distillate from line 16 was condensed into water and discarded as it is.
(c) Caprolactam was extracted in step 3 with benzene from line 19.
(d) Sulfur element (50Kg/h) and air 300(Nm³/h) were fed to the combustion step 4 to carry out combustion treatment.
(e) The sulfur dioxide containing gas (conc. 12 vol.%) from line 11 was oxidized by conventional method into sulfuric anhydride, followed by conversion into fuming sulfuric acid, and used in the rearrangement step of cyclohexanone oxime.

What we claim is:

1. A process for producing caprolactam by effecting Beckmann rearrangement of cyclohexanone oxime with a concentrated sulfuric acid or fuming sulfuric acid, neutralizing the rearranged mixture with ammonia and separating ammonium sulfate and caprolactam from the neutralized product, wherein the improvement comprises treating process waste waters after separation of said ammonium sulfate and caprolactam in accordance with the following steps:

(1) first concentrating by distillation at a temperature in the range from 80° to 130° C under a pressure in the range from 400 mm Hg to 2.7 Kg/cm² to a water concentration in the range from 85 to 75 wt.%;

(2) then further concentrating by distillation of the concentrate at a temperature in the range from 40° to 80° C under a pressure in the range from 50 to 400 mm Hg to a water concentration in the range from 70 to 15 wt.%;

(3) extracting the caprolactam from the thus obtained concentrate at a pH controlled to a pH between 2.5 and 6 with an aromatic hydrocarbon as an extraction solvent thereby to recover the caprolactam;

(4) conducting oxidative combustion of the extraction residue at a temperature in the range from 800° to 1300° C; and, (5) converting the thus formed sulfur dioxide to sulfuric acid.

2. A process according to claim 1 wherein the combustion is carried out by employing sulfur and oxygen or a molecular oxygen containing gas.

3. A process as claimed in claim 1, wherein the organic solvent contained in the distillate obtained in the step (1) is recovered.

4. A process as claimed in claim 1, wherein the sulfuric acid obtained in the step (5) is recycled to the step of the rearrangement.

5. A process as claimed in claim 1, wherein the organic solvent contained in the distillate obtained in the step (1) is recovered and the sulfuric acid obtained in the step (5) is recycled to the step of the rearrangement.

6. A process as claimed in claim 5, wherein the aromatic hydrocarbon is benzene or toluene.

7. A process as claimed in claim 5, wherein sulfur dioxide contained in the distillate from the step (1) is subjected to combustion treatment by being absorbed in the waste waters to be fed into the combustion step (4).

8. A process as claimed in claim 5, wherein sulfur dioxide contained in the distillate from the step (1) is converted to sulfuric acid by being incorporated into the gas discharged from the combustion step (4).

9. A process as claimed in claim 1, wherein the distillate from the step (1) is utilized as heat source for the step (2).

* * * * *